(12) United States Patent
Galperin et al.

(10) Patent No.: US 9,192,402 B2
(45) Date of Patent: Nov. 24, 2015

(54) RETRIEVAL BASKET APPARATUS

(71) Applicant: Gyrus ACMI, Inc., Southborough, MA (US)

(72) Inventors: Nison Galperin, Fairfield, CT (US); Carlo A. DiRusso, Bronx, NY (US)

(73) Assignee: Gyrus ACMI, Inc., Southborough, MA (US)

( * ) Notice: Subject to any disclaimer, the term of this patent is extended or adjusted under 35 U.S.C. 154(b) by 159 days.

(21) Appl. No.: 13/715,091

(22) Filed: Dec. 14, 2012

(65) Prior Publication Data

US 2014/0171735 A1  Jun. 19, 2014

(51) Int. Cl.
| | | |
|---|---|---|
| *A61B 1/00* | (2006.01) | |
| *A61B 17/221* | (2006.01) | |
| *A61B 1/018* | (2006.01) | |
| *A61B 1/307* | (2006.01) | |
| *A61B 17/29* | (2006.01) | |
| *A61B 1/04* | (2006.01) | |
| *A61B 17/00* | (2006.01) | |

(52) U.S. Cl.
CPC ............ *A61B 17/221* (2013.01); *A61B 1/00066* (2013.01); *A61B 1/00096* (2013.01); *A61B 1/018* (2013.01); *A61B 1/307* (2013.01); *A61B 17/2909* (2013.01); *A61B 2017/00367* (2013.01); *A61B 2017/00424* (2013.01); *A61B 2017/2212* (2013.01); *A61B 2017/2916* (2013.01); *A61B 2017/2923* (2013.01); *Y10T 29/49826* (2015.01)

(58) Field of Classification Search
CPC ........... A61B 1/00066; A61B 1/00096; A61B 1/018; A61B 1/00085
USPC ................. 600/104, 106, 107, 131, 102, 153; 606/127, 128, 205; 348/45, 65
See application file for complete search history.

(56) References Cited

U.S. PATENT DOCUMENTS

| | | | | |
|---|---|---|---|---|
| 5,397,304 | A | * | 3/1995 | Truckai .......................... 604/528 |
| 5,403,324 | A | * | 4/1995 | Ciervo et al. ................. 606/127 |
| 5,573,530 | A | | 11/1996 | Fleury et al. ...................... 606/1 |
| 5,921,956 | A | | 7/1999 | Grinberg et al. ................ 604/95 |
| 6,764,499 | B2 | | 7/2004 | Honey et al. ................... 606/207 |
| 7,615,003 | B2 | | 11/2009 | Stefanchik et al. ............ 600/104 |
| 7,691,103 | B2 | | 4/2010 | Fernandez et al. ............... 606/41 |
| 7,775,968 | B2 | | 8/2010 | Mathis .......................... 600/104 |
| 7,815,565 | B2 | | 10/2010 | Stefanchik et al. ............ 600/121 |
| 7,857,754 | B2 | | 12/2010 | Spivey et al. ................... 600/127 |
| 7,905,830 | B2 | | 3/2011 | Stefanchik et al. ............ 600/121 |
| 7,922,650 | B2 | | 4/2011 | McWeeney et al. ........... 600/104 |
| 8,211,115 | B2 | | 7/2012 | Cheng et al. ................... 606/114 |
| 2003/0023247 | A1 | | 1/2003 | Lind et al. ...................... 606/127 |
| 2008/0188890 | A1 | * | 8/2008 | Weitzner et al. ............... 606/205 |
| 2009/0157060 | A1 | * | 6/2009 | Teague et al. ..................... 606/1 |
| 2011/0178388 | A1 | | 7/2011 | Kuhara et al. ................. 600/411 |

\* cited by examiner

*Primary Examiner* — Anhtuan T Nguyen
*Assistant Examiner* — Timothy J Neal
(74) *Attorney, Agent, or Firm* — Harrington & Smith

(57) ABSTRACT

An object removal tool including a basket device having a basket section; a sheath on the basket device, where the sheath is adapted to longitudinally slide on the basket device; and a control connected to the basket device and the sheath. The control is configured to longitudinally move the sheath on the basket device to close the basket section on an object.

10 Claims, 5 Drawing Sheets

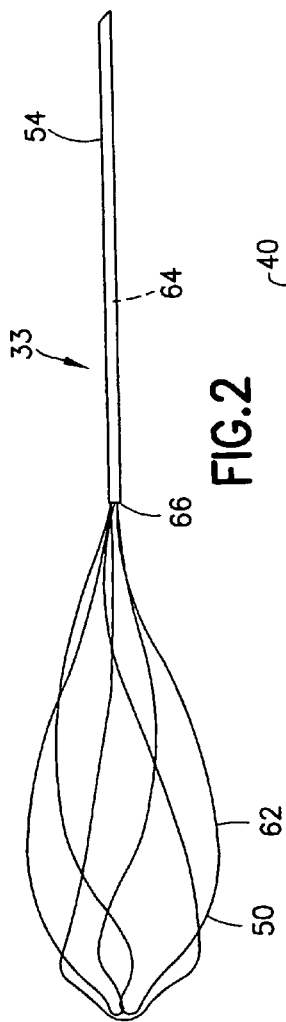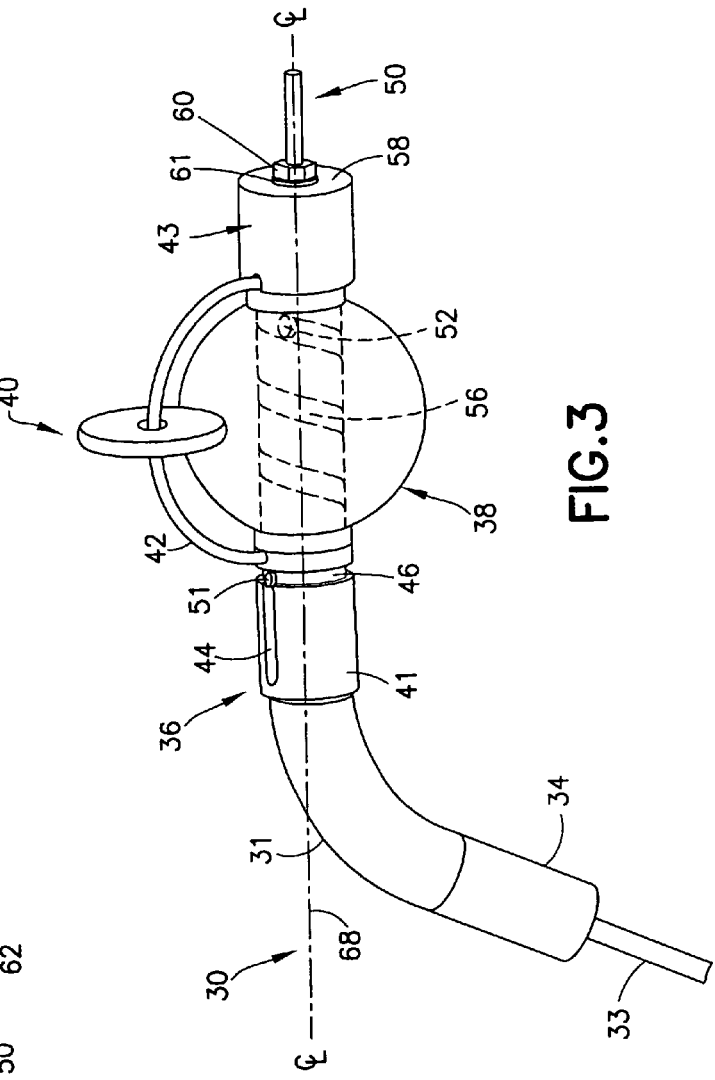

RETRIEVAL BASKET APPARATUS

BACKGROUND

1. Technical Field

The exemplary and non-limiting embodiments relate generally to a device having a basket and, more particularly, to a method and apparatus for a closable basket.

2. Brief Description of Prior Developments

U.S. Pat. No. 6,764,499 discloses a medical device with a basket. U.S. Pat. No. 8,211,115 discloses a variable size retrieval basket.

SUMMARY

The following summary is merely intended to be exemplary. The summary is not intended to limit the scope of the claims.

In accordance with one aspect, an object removal tool is provided comprising a basket device comprising a basket section; a sheath on the basket device, where the sheath is adapted to longitudinally slide on the basket device; and a control connected to the basket device and the sheath. The control is configured to longitudinally move the sheath on the basket device to close the basket section on an object.

In accordance with another aspect, an apparatus comprises an endoscope having a shaft with a lens at a distal end; and an object removal tool connected to a port of the endoscope. The object removal tool comprises a basket device and a control. The basket device comprises a basket section for capturing an object. The control is configured to close the basket section around the object. The endoscope and the control are configured to be used by a single hand of a user at a same time.

In accordance with another aspect, a method comprises connecting an object removal tool to an endoscope including inserting a portion of the object removal tool into a port of the endoscope; and rotating a sheath of the object removal tool to cause the sheath to longitudinally slide relative to the basket device.

In accordance with another aspect, a method comprises connecting a sheath to a basket device for longitudinal only movement on the basket device in the sheath, where a distal end of the basket device comprises a basket section; connecting a proximal end of the basket device to a bracket; connecting the bracket to a holder, where the bracket is limited to longitudinally slide along a first length of travel of the bracket on the holder and is rotatable on the holder at an end of the first length of travel, where the holder is configured to connect to a port of an endoscope; and connecting the sheath to a cam where the cam is configured to longitudinally move the sheath when the sheath and the cam are rotated relative to each other.

BRIEF DESCRIPTION OF THE DRAWINGS

The foregoing aspects and other features are explained in the following description, taken in connection with the accompanying drawings, wherein:

FIG. 2 is a side view of a distal end of an assembly comprising a sheath and a basket device;

FIG. 3 is a side view of the control of the tool shown in FIG. 1;

DETAILED DESCRIPTION OF EMBODIMENTS

Figure 1:
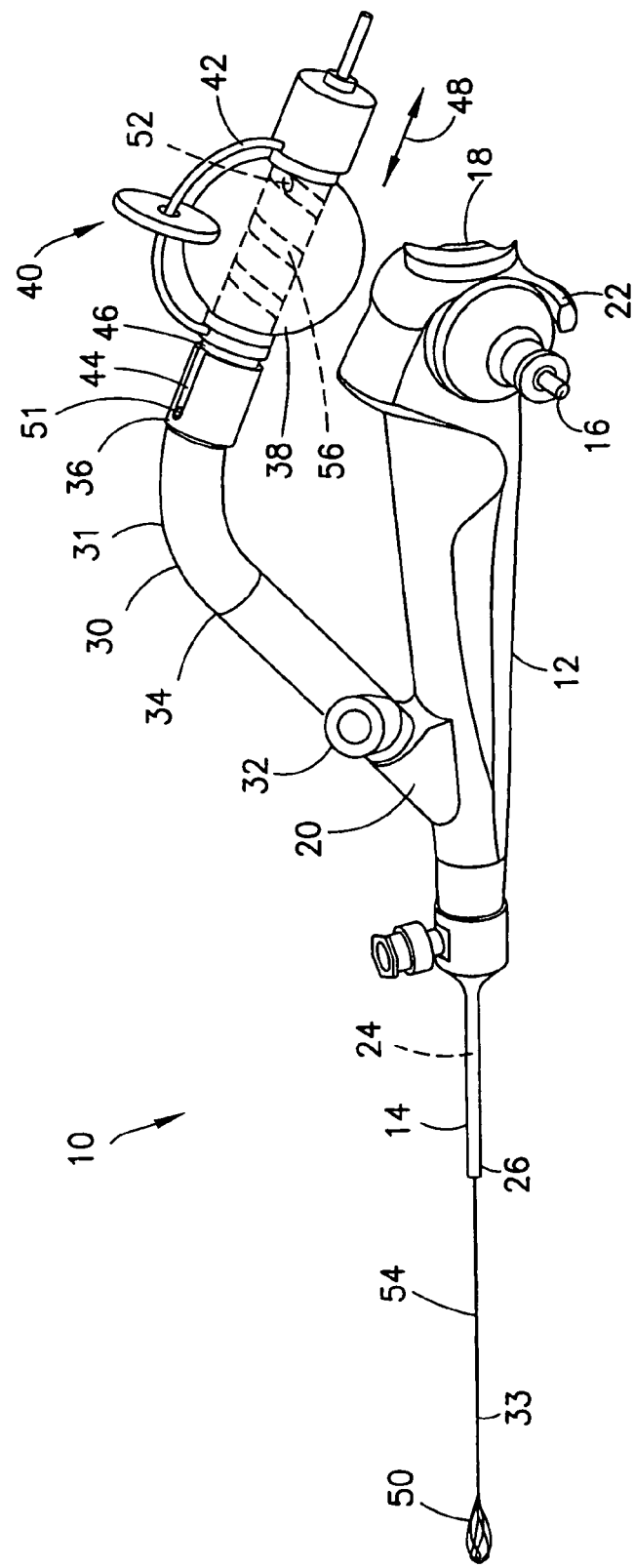
FIG. 1 is a perspective view of an example embodiment.

Referring to FIG. 1, there is shown a perspective view of an apparatus 10 and tool 30 incorporating features of an example embodiment. Although the features will be described with reference to the example embodiment shown in the drawings, it should be understood that features can be embodied in many alternate forms of embodiments. In addition, any suitable size, shape or type of elements or materials could be used.

The apparatus 10 in this example is a endoscope medical device configured to be partially inserted into a patient's body, such as in through the patient's urethra. The apparatus 10 generally comprises a control section 12 and a shaft 14. The control section 12 is sized and shaped to be grasped by the user's hand. In the example embodiment shown, the control section 12 includes a connector 16 which is a fiber optics light post. The light post 16 may be connected to a light source. Features as described herein may be configured to work with a fiber optic endoscope or a digital endoscope. The apparatus may comprise an eyepiece (see FIGS. 6-9) at a proximal end 18 of the control section 12. The apparatus has a working channel port 20, and a deflection control 22 lever. However, in alternate embodiments any suitable type of control section could be provided.

The shaft 14 extends from the control section 12 in a general cantilever fashion. A distal end of the shaft 14 may comprise optics forming an objective head, such as a lens and/or camera. The shaft 14 includes a working channel 24 from the working channel port 20. The working channel 24 allows fluids, tools and tissue or stones to be passed through the shaft 14. The distal end of the shaft 14 has an aperture out of the working channel 24. The shaft 14 may include fiber optics or electrical wires to the optics in the distal tip, such as for illumination and/or visualization, and deflection control wires are provided in the shaft between the deflection control lever 22 and a frame of an active deflection section 26 of the shaft 14.

In this example, the apparatus 10 comprises a Y-adapter 32 attached to the working channel port 20 for attaching standard connector and additional instruments if needed. However, in an alternate example the Y-adapter 32 might not be provided, or may be integrally formed with the endoscope 10. A device or tool 30 is shown attached to the working channel port 20 of the endoscope 10 via the Y-adapter 32. The tool 30, in this example, is a Surgeon Controlled Basket Device (SCBD). The tool 30 includes a control 31 and an assembly 33.

The assembly 33 generally comprises a basket device 50 and a sheath 54. Referring also to FIG. 2, the basket device 50 comprises a basket section 62 at a distal end, and a shaft section 64 extending through the sheath 54 to a proximal end of the tool 30. The sheath is longitudinally movable on the basket device 50 between a forward position and a rearward position. FIG. 2 shows the sheath 54 moved rearward on the basket device 50 to the rearward position such that the basket section is located out from a front end aperture 66 of the sheath 54. In the forward position of the sheath 54 on the basket device 50, the basket section 62 is located inside the sheath 54; collapsed by the sheath 54 into a smaller shape to fit inside the sheath 54.

Figure 4:
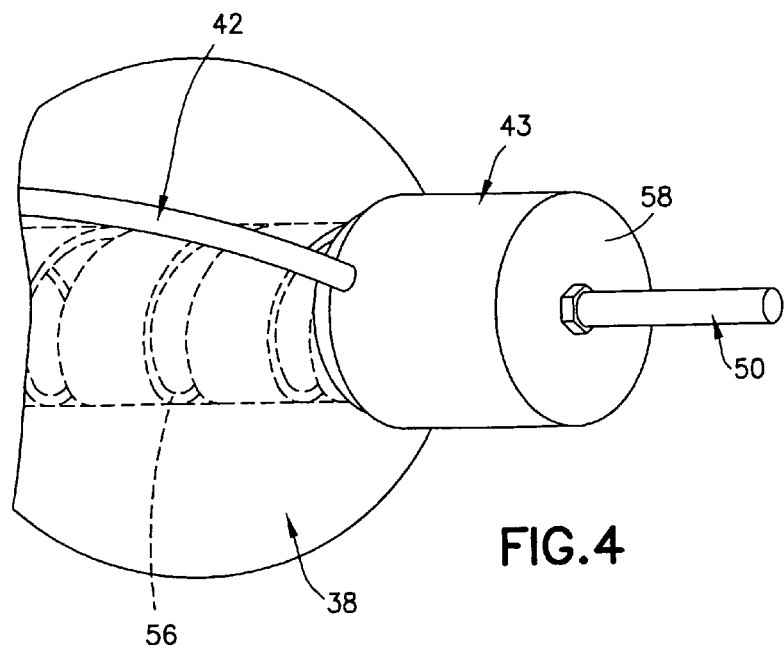
FIG. 4 is a partial perspective view of a proximal end of the tool shown in FIG. 1.
Figure 5:
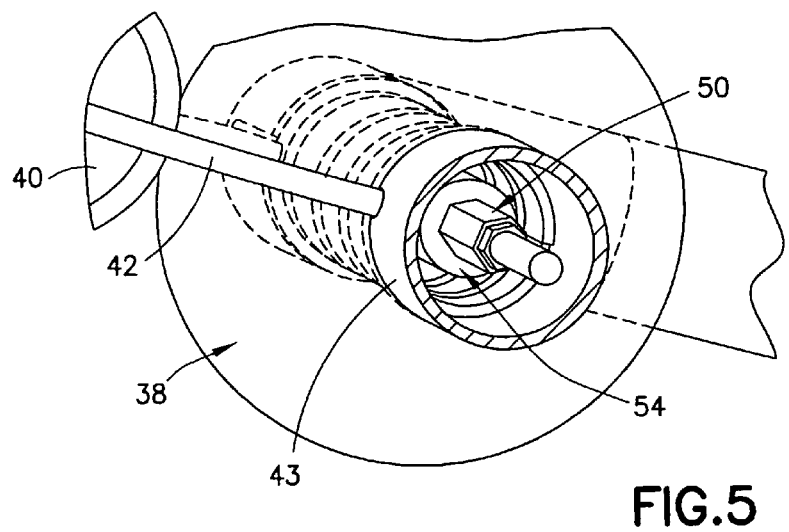
FIG. 5 is a partial perspective view with a cut away section of the proximal end of the tool shown in FIG. 4.
Figure 7:
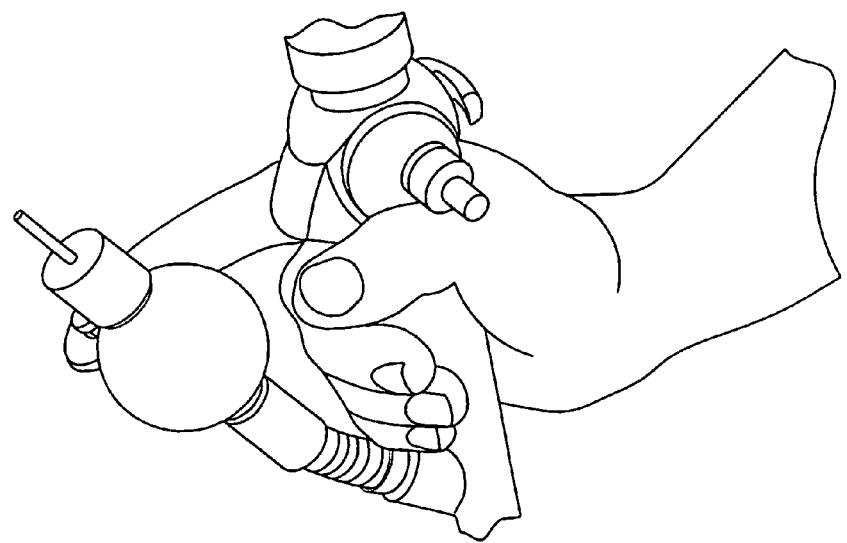
FIGS. 6-9 are perspective views illustrating how a user may hold and use the example embodiment with one hand.
Figure 6:
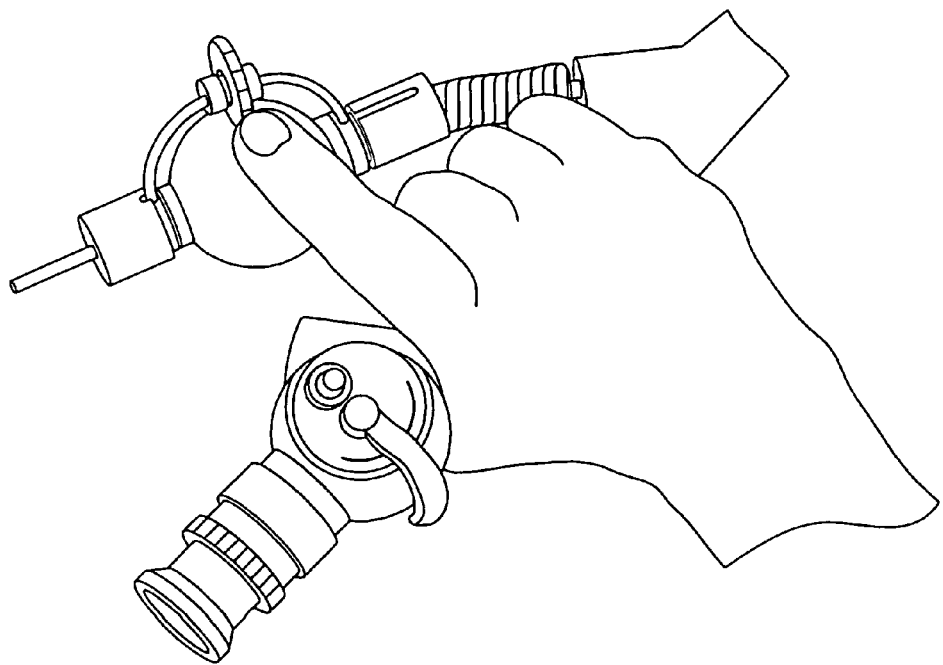
Figure 9:
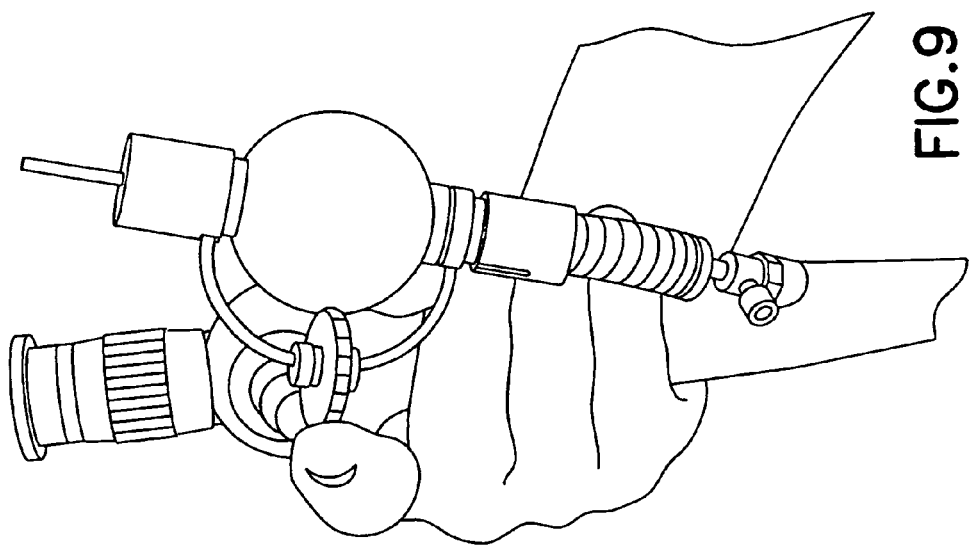
Figure 8:
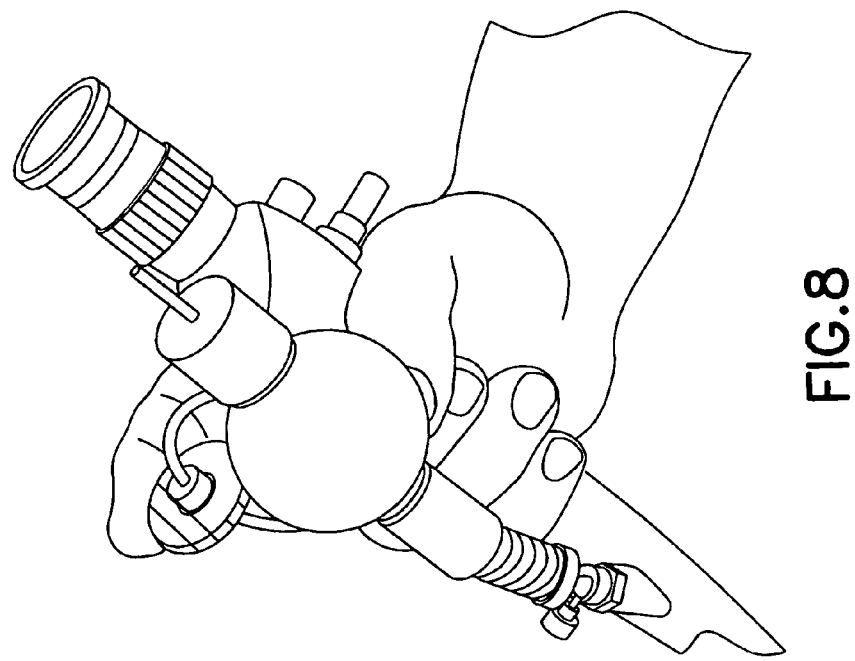

Referring also to FIGS. 3-5, the control 31 generally comprises a holder 34, a bracket 36, a cam 38, and a control wheel 40. The holder 34 is adapted to connect the control 31 to the working channel port 20 (or the Y-adapter 32 in this example).

In this example the holder 34 comprises an adjustable gooseneck design which is flexible. This allows adjusting the control 31 to adapt to the hand size of the surgeon using the tool. The bracket 36 is movable connected to the holder 34. The bracket 36 comprises a front section 41, a rear section 43 and a curved connector section 42. Bracket 36 is connected to two opposite ends of the cam 38. In particular, the cam 38 is connected between the front and rear sections 41, 43. The cam 38 can freely be rotated around the axis 68.

The control wheel 40 is mounted on the curved connector 42 and is axially rotatable on the connector 42. The control wheel 40 contacts the cam 38 and may provide transfer of a surgeon's manual rotation of the wheel 40 to the cam 38. The front section 41 of the bracket 36 has two slots 44, 46 which intersect and are perpendicular to each other. Slot 44 is parallel to the rotation axis 68 and allows the surgeon to move the bracket 36 forward and backward on the holder 34 as indicated by arrow 48. The perpendicular slot 46 allows for rotating the bracket 36 during a surgical procedure after the bracket 36 has been moved to a forward position on the holder 34. Both slots 44, 46 work with a pin 51 located on the proximal end of the holder 34.

A proximal cylindrical end of the sheath 54 of the assembly 33 extends into the cam 38. This sheath 54 has a pin 52. The pin 52 is located in an internal spiral surface 56 of the cam 38. The proximal cylindrical end of sheath 54 has an internal hexagon cut. As best seen in FIG. 5, the proximal end of the shaft section 64 of the basket device 50 has an outside hexagon surface. The outside hexagon surface of the proximal end of the shaft section 64 is matingly located inside the internal hexagon cut of the proximal end of the sheath 54. This constraint allows for a longitudinal reciprocating motion of the sheath 54 relative to the basket device 50, but limits or prevents axial rotation of the sheath 54 relative to the basket device 50. The proximal end of the basket device 50 is fixed with a cap and locked with nut 60 with washer 61 to the rear section 43 of the bracket 36. A hexagon opening prevents the basket device 50 from axially rotating relative to the rear section 43 of the bracket 36.

The sheath 54 is assembled with the basket device 50, and the assembly 33 is inserted into a back opening of the cam 38. Sheath 54 turns along the functional curve 56 of the cam 38 and moves ahead to a maximum distal position. The basket device 50 will stay inside the sheath 54. The assembled cap 58 and nut 60 with washer 61 prevents the basket device 50 from rotation and secure the basket device 50 against motion along the axis 30 relative to the bracket 36. After that, the assembled tool 30 can be attached to the endoscope working channel port 20 or Y-adapter in this example) by inserting the proximal end of the basket device 50 and sheath 54 into the working channel of the endoscope.

After the distal end of the assembly 33 is located at a suitable location to perform a task, the bracket 36 may be moved forward along the longitudinal slot 44 on the distal ring 41 of the bracket 36. With this movement both the sheath 54 with the basket device will move out from inside of the working channel forward past the distal end aperture of the shaft 14. In this position the tool 30 is ready for use and the user can work with the tool (such as using only one hand) to capture fragments of kidney stones. The user may rotate the cam 38, such as by rotating the wheel 40. Rotation of the cam 38 causes the bracket 36 to rotate with slot 46 moving relative to pin 51. The pin 52 on the sheath moves in the spiral surface 56. This causes the sheath 54 to longitudinally slide rearward on the basket device 50. Because of the relative longitudinal movement of the sheath rearward on the basket device 50, the basket section 62 is uncovered from being inside the sheath 54, and the basket section 62 springs into the shape shown in FIG. 2. The user may then manipulate the basket section 62 to locate the fragments into the basket section 62. Now, the user may rotate the cam 38 in an opposite direction of rotation. This will cause the bracket 36 to rotate in an opposite direction with the slot 46 moving relative to pin 51. The pin 52 on the sheath 54 moves in the spiral surface 56. This causes the sheath 54 to longitudinally slide forward on the basket device 50. The sheath 54, thus, is slid forward to cause the basket section 62 to partially close and capture the fragments inside the basket section 62. The user may then withdraw the assembly 33, remove the fragments from the assembly 33, and repeat the process to remove all the fragments to be removed. Rotating the cam 38 around its own axis longitudinally moves the sheath 54 forward and back for closing and opening basket section 62. FIGS. 6-9 are perspective views showing how the user may hold the endoscope and use the tool with only one hand; using the wheel or the cam directly.

Features as described herein may be used in an endoscope, such as with lithotripsy, a kidney stone retaining basket, a grasper and/or a clip-on basket. Urology lithotripsy and surgery processes require using grasping or biopsy forceps and a retaining basket which operates by control wire that extends through a sheath. Most existing instruments have a slider which moves along a handle operating the device with a sliding motion and locking mechanism. Existing devices are designed for using two hands during the operation. For additional manipulations (irrigation, changing accessories . . . ), the surgeon requires some help from a medical assistant or nurse because, in this case, both his hands are holding the endoscope and the basket manipulation device. This means that a minimum of two specialists must be involved in this procedure. In the process of "fishing" and capturing fragments of a kidney stone, the fragments are very often lost when the basket closes. This happens because the basket is moving back and the sheath is fixed.

The example embodiment described above may be used for one hand manipulation of the endoscope and basket control device. The surgeon can hold both the endoscope and the basket control device using only one hand. The second hand can be used for additional manipulation, such as changing and adjusting accessories and irrigation using a syringe or liquid container adapter valve. The surgeon can do the entire procedure without support of an additional specialist. The device allows the sheath to move with a fixed basket during open-close procedure. This feature reduces the possibility of losing fragments of stones during the basket closing process.

Features as described above may be used in a hand-operated surgical instrument and, more particularly, to a device which provides a control mechanism for a stone basket for use with an endoscope allowing the surgeon to use a single hand during the operation procedure. The ergonomic design of this device allows the surgeon to manipulate the device and endoscope with a single hand. The surgical instrument can be used for biopsy and grasping forceps, or a retaining basket and potentially for laser probe and guide wires. The additional port from the Y-adapter allows irrigation and using a guide wire or laser without detaching this device from the endoscope irrigation port. In addition, the device allows for moving the sheath with a fixed basket during open-close procedure. This feature, longitudinally moving the sheath rather than longitudinally moving the basket to close the basket, reduces the possibility of losing fragments of stones during the basket closing process.

In one example embodiment, an object removal tool comprises a basket device 50 comprising a basket section 62; a sheath 54 on the basket device, where the sheath is adapted to longitudinally slide on the basket device; and a control 31 connected to the basket device and the sheath, where the control is configured to longitudinally move the sheath 54 on the basket device 50 to close the basket section 62 on an object, and where the control comprises a cam member 38 having a cam surface 56 adapted to cam against a portion 52 of the sheath as the sheath and the cam member are rotated relative to each other.

The control may comprise a holder 34 configured to be removably connected to a port of an endoscope and a bracket 36 movably connected to the holder, where a proximal end of the basket device is fixedly connected to the bracket. The bracket may be limited to longitudinal sliding movement along a first length of travel of the bracket on the holder and may be rotatable on the holder at an end of the first length of travel. The cam member may be connected to the bracket, where the bracket is configured to axially rotate relative to the cam member. The sheath may comprise a portion which is located in a cam slot inside the cam member. The bracket may comprises a first portion in front of the cam member, a second portion behind the cam member, a connection section which connects the first and second portions to each other, and a rotatable member 40 on the connection section which contacts the cam member and is configured to rotate on the connection section and the cam member.

In an example embodiment an apparatus may comprise an endoscope having a shaft with a lens at a distal end; and an object removal tool connected to a port of the endoscope, where the object removal tool comprises a basket device and a control, where the basket device comprises a basket section for capturing an object, and where the control is configured to close the basket section around the object, where the endoscope and the control are configured to be used by a single hand of a user at a same time.

The object removal tool may comprise a sheath on the basket device, where the sheath is adapted to longitudinally slide on the basket device, and where the control comprises a cam member having a cam surface adapted to cam against a portion of the sheath as the sheath and cam member are rotated relative to each other. The control may comprise a holder configured to be removably connected to a port of an endoscope and a bracket movably connected to the holder, where a proximal end of the basket member is fixedly connected to the bracket, where the bracket is limited to longitudinally slide along a first length of travel of the bracket on the holder and is rotatable on the holder at an end of the first length of travel, where the sheath comprises a portion which is located in a cam slot inside the cam member, and where the bracket comprises a first portion in front of the cam member, a second portion behind the cam member, a connection section which connects the first and second portions to each other, and a rotatable member on the connection section contacts the cam member and is configured to rotate on the connection section and the cam member An example method may comprise connecting an object removal tool to an endoscope including inserting a portion of the object removal tool into a port of the endoscope; and rotating a sheath of the object removal tool to cause the sheath to longitudinally slide relative to the basket device. Rotating a sheath to cause the sheath to longitudinally slide relative to the basket device may comprise rotating a cam member and the sheath relative to each other while preventing axial rotation of the basket device relative to the sheath. Connecting the object removal tool to the endoscope may comprise connecting a holder of the object removal tool to the port, and inserting the sheath and the basket device through the port into a shaft of the endoscope, and the method further comprises longitudinally sliding a bracket of a control of the object removal tool forward on the holder to move distal ends of the sheath and the basket device out of a distal end of the shaft, and then axially rotating the bracket to cause the sheath to both rotate with the basket device and longitudinally slide on the basket device.

An example method may comprise connecting a sheath to a basket device for longitudinal only movement on the basket device in the sheath, where a distal end of the basket device comprises a basket section; connecting a proximal end of the basket device to a bracket; connecting the bracket to a holder, where the bracket is limited to longitudinally slide along a first length of travel of the bracket on the holder and is rotatable on the holder at an end of the first length of travel, where the holder is configured to connect to a port of an endoscope; and connecting the sheath to a cam where the cam is configured to longitudinally move the sheath when the sheath and the cam are rotated relative to each other. The method may further comprise connecting the holder to the port of the endoscope such that the bracket is located to be axially rotated by a single hand of a user at a same time that the user is holding the endoscope in the same hand.

Features as described above are not limited to use with a retrieval basket. Features as described above may be used to manipulate any suitable type of endoscope accessory. The endoscope accessory may be a retrieval basket, or a laser probe, or an electrode, or a guide wire for example.

In accordance with another example, an apparatus 10 may comprise an endoscope having a shaft with a lens at a distal end; and a tool connected to a port of the endoscope, where the tool comprises a control and an endoscope accessory portion connected to the control, where the endoscope accessory portion comprises extends from the port, through a working channel of the shaft, to a distal end aperture out of the shaft, and where the control is configured to move the endoscope accessory portion out of the distal end aperture, where the endoscope and the control are configured to be used by a single hand of a user at a same time. The tool may be an object removal tool, where the endoscope accessory portion comprises a basket device comprising a basket section adapted to capture an object, and where the control is configured to close the basket section around the object.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications and variances which fall within the scope of the appended claims.

What is claimed is:

1. An object removal tool comprising:
   a basket device comprising a basket section;
   a sheath on the basket device, where the sheath is adapted to longitudinally slide on the basket device; and
   a control connected to the basket device and the sheath, where the control is configured to longitudinally move the sheath on the basket device to close the basket section on an object,
   where the control comprises a cam member having a cam surface adapted to cam against a portion of the sheath as the sheath and the cam member are rotated relative to each other,
   where the cam member is configured to longitudinally move the sheath while a proximal end of the basket device remains substantially stationary, where the cam member rotates a helix which translates the rotational motion to longitudinal motion via a pin, where the pin is connected to the sheath, where the pin extends into a cutout portion of the helix.

2. The object removal tool of claim 1 where the control comprises a holder configured to be removably connected to a port of an endoscope and a bracket movably connected to the holder, where a proximal end of the basket device is fixedly connected to the bracket.

3. The object removal tool of claim 2 where the bracket is limited to longitudinal sliding movement along a first length of travel of the bracket on the holder and is rotatable on the holder at an end of the first length of travel.

4. The object removal tool of claim 2 where the cam member is connected to the bracket, where the bracket is configured to axially rotate relative to the cam member.

5. An apparatus comprising:
an endoscope having a shaft with a lens at a distal end; and
an object removal tool as in claim 1 connected to a port of the endoscope.

6. An apparatus comprising:
an endoscope having a shaft with a lens at a distal end;
a tool connected with a holder to a port of the endoscope, where the tool comprises a basket device and a sheath surrounding the basket device, where the basket device and the sheath extend from the port, through a working channel of the shaft, to a distal end aperture out of the shaft;
a bracket, where the bracket is movably connected to the holder, where the bracket comprises a front section, a rear section, and a connector section;
a control comprising a control wheel, where the control is configured to open the basket device out of the distal end aperture, the control comprising a cam member having a cam surface adapted to cam against a portion of the sheath as the sheath and cam member are rotated relative to each other;
where the endoscope and the control are configured to be used by a single hand of a user at a same time,
where the holder is an adjustable gooseneck holder, where the holder can be adjusted to adapt to a hand size of a user, where a proximal cylindrical end of the sheath has an internal hexagon cut and where the proximal end of the shaft has an outside hexagon surface.

7. The apparatus of claim 6, where the outside hexagon surface of the shaft is matingly engaged with the internal hexagon cut of the sheath allowing for longitudinal reciprocating motion of the sheath relative to the basket but limiting axial rotation of the sheath relative to the basket device.

8. The apparatus of claim 6, where the proximal end of the basket device is fixed with a cap and locked with a nut and washer to the rear section of the basket to prevent rotation of the basket device.

9. The apparatus of claim 6, where rotation of the cam causes the sheath to turn along a functional curve to advance and retract longitudinally.

10. An apparatus comprising:
an endoscope having a shaft with a lens at a distal end;
a tool connected with a holder to a port of the endoscope, where the tool comprises a basket device and a sheath surrounding the basket device, where the basket device and the sheath extend from the port, through a working channel of the shaft, to a distal end aperture out of the shaft;
a bracket, where the bracket is movably connected to the holder, where the bracket comprises a front section, a rear section, and a connector section;
a control comprising a control wheel, where the control is configured to open the basket device out of the distal end aperture, the control comprising a cam member having a cam surface adapted to cam against a portion of the sheath as the sheath and cam member are rotated relative to each other;
where the endoscope and the control are configured to be used by a single hand of a user at a same time,
where the holder is an adjustable gooseneck holder, where the holder can be adjusted to adapt to a hand size of a user, where rotation of the cam causes the bracket to rotate with a slot moving relative to a pin, where the pin is attached to the sheath.

\* \* \* \* \*